US010779723B2

(12) United States Patent
Huang et al.

(10) Patent No.: US 10,779,723 B2
(45) Date of Patent: Sep. 22, 2020

(54) VISUAL NEUROMODULATION SYSTEM AND METHODS FOR TREATMENTS OF VISUALLY TRIGGERED MIGRAINE HEADACHES AND SEIZURES

(71) Applicant: Board of Trustees of Michigan State University, East Lansing, MI (US)

(72) Inventors: Jie Huang, Okemos, MI (US); David C. Zhu, Haslett, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 164 days.

(21) Appl. No.: 16/182,218

(22) Filed: Nov. 6, 2018

(65) Prior Publication Data

US 2019/0133438 A1  May 9, 2019

Related U.S. Application Data

(60) Provisional application No. 62/582,535, filed on Nov. 7, 2017.

(51) Int. Cl.
*A61B 3/02* (2006.01)
*A61B 3/06* (2006.01)
(Continued)

(52) U.S. Cl.
CPC ............ *A61B 3/063* (2013.01); *A61B 3/0033* (2013.01); *A61B 3/0041* (2013.01); *A61H 1/00* (2013.01);
(Continued)

(58) Field of Classification Search
CPC .......... A61B 3/032; A61B 3/036; A61B 3/063
(Continued)

(56) References Cited

U.S. PATENT DOCUMENTS

| 4,365,873 | A | 12/1982 | Ginsburg |
| 8,979,263 | B2 | 3/2015 | Lawton |
| 2015/0201832 | A1* | 7/2015 | Palanker ............... A61B 3/0058 |
| | | | 351/239 |

OTHER PUBLICATIONS

Huang, J. & Zhu, D. C. (2017). Visually Stressful Striped Patterns Alter Human Visual Cortical Functional Connectivity. Wiley Periodicals, Inc., 11 pages.

* cited by examiner

*Primary Examiner* — Hung X Dang
(74) *Attorney, Agent, or Firm* — Harness, Dickey & Pierce, P.L.C.

(57) ABSTRACT

A visual neuromodulation system includes a processor and a transition function determination module configured to determine a spatial frequency transition function corresponding to a spatial frequency based on user input. The user input includes: (i) a quantity of illusions perceived in response to viewing a spatial frequency pattern associated with the spatial frequency and (ii) a level of discomfort sensed in response to viewing the spatial frequency pattern associated with the spatial frequency. The system also includes a threshold determination module configured to determine a threshold spatial frequency based on the spatial frequency transition function. The system includes, in response to the threshold determination module determining the threshold spatial frequency, a control module that selects a display spatial frequency pattern from a set of spatial frequency patterns. The selected spatial frequency pattern corresponds to a display spatial frequency greater than the threshold spatial frequency to display for a predetermined period.

20 Claims, 6 Drawing Sheets

(51) Int. Cl.
*A61B 3/00* (2006.01)
*A61H 5/00* (2006.01)
*A61H 1/00* (2006.01)
A61B 5/00 (2006.01)
G06F 3/0481 (2013.01)

(52) U.S. Cl.
CPC .............. *A61H 5/00* (2013.01); *A61B 5/4884* (2013.01); *A61H 2201/5007* (2013.01); *A61H 2201/5043* (2013.01); *A61H 2201/5046* (2013.01); *A61H 2205/024* (2013.01); *G06F 3/0481* (2013.01)

(58) Field of Classification Search
USPC ........ 351/203, 239, 246, 240, 241, 242, 243
See application file for complete search history.

VISUAL NEUROMODULATION SYSTEM AND METHODS FOR TREATMENTS OF VISUALLY TRIGGERED MIGRAINE HEADACHES AND SEIZURES

CROSS-REFERENCE TO RELATED APPLICATIONS

This application claims the benefit of U.S. Provisional Application No. 62/582,535, filed Nov. 7, 2017. The entire disclosure of the application referenced above is incorporated by reference.

FIELD

The present disclosure relates to visual neuromodulation systems and methods, and, more specifically, executing a visual neuromodulation system on a computing device.

BACKGROUND

This section provides background information related to the present disclosure which is not necessarily prior art.

More than 37 million people suffer from migraines in the U.S. alone, which accounts for about 13% of the population. A survey reported that 91% of people miss work or cannot function during a migraine attack and 70% reported relationship issues due to migraine attacks. Migraines are a debilitating neurological disorder that affects nerve pathways and brain chemicals for a period of anywhere from 4 to 72 hours at a time. A quarter of all migraines include aura, which is a distinct warning sign that a migraine is coming. Aura is typically visual and can create alterations and distortions in vision. Although not all migraines contain aura, most are associated with photophobia or visual discomfort. Bright light, flickering light, and certain visual patterns have been identified as major migraine triggers, though stress is the most common headache trigger. In migraine patients, the visual discomfort threshold is significantly lower than in non-migraine patients. Visual cortical hyperexcitability (VCH) is thought to be responsible for visually triggered headaches, and a reduced VCH may result in a reduced headache frequency.

SUMMARY

A visual neuromodulation system includes a processor and a transition function determination module configured to determine a spatial frequency transition function corresponding to a spatial frequency based on user input. The user input includes: (i) a quantity of illusions perceived in response to viewing a spatial frequency pattern associated with the spatial frequency and (ii) a level of discomfort sensed in response to viewing the spatial frequency pattern associated with the spatial frequency. The system also includes a threshold determination module configured to determine a threshold spatial frequency based on the spatial frequency transition function. The system includes, in response to the threshold determination module determining the threshold spatial frequency, a control module that selects a display spatial frequency pattern from a set of spatial frequency patterns. The selected spatial frequency pattern corresponds to a display spatial frequency greater than the threshold spatial frequency to display for a predetermined period.

In other aspects, the system includes a spatial frequency pattern database. In other aspects, the control module is configured to obtain the selected spatial frequency pattern corresponding to the display spatial frequency from the spatial frequency pattern database. In other aspects, the system includes a storage module configured to maintain an index. In other aspects, each entry of the index includes: (i) a previous user identifier, (ii) a most recent user input of a previous user corresponding to the previous user identifier, and (iii) a most recent selected spatial frequency of the previous user. In other aspects, the control module obtains a most recent selected spatial frequency of a present user from the storage module and selects a corresponding most recent selected spatial frequency pattern from a spatial frequency pattern database. In other aspects, the transition function determination module, the threshold determination module, the control module, and the storage module are separate processor circuits that execute code.

In other aspects, in response to a new user indicator indicating a present user is new, the control module selects a beginning spatial frequency pattern as the spatial frequency pattern. In other aspects, in response to an index entry corresponding to a present user identifier of the present user being included in the storage module, the control module sets a most recent selected spatial frequency as the spatial frequency, selects a most recent selected spatial frequency pattern corresponding to the most recent selected spatial frequency, and displays the most recent selected spatial frequency pattern for the predetermined period. In other aspects, the new user indicator indicates the present user is new when the storage module excludes the index entry corresponding to the present user identifier of the present user. In other aspects, the beginning spatial frequency pattern is displayed for a beginning predetermined period.

In other aspects, in response to a new user indicator indicating a present user is new, a control module cycles through a beginning set of spatial frequency patterns. In other aspects, the cycling includes: displaying each spatial frequency pattern included in the beginning set of spatial frequency patterns for the predetermined period and receiving user input for each spatial frequency pattern included in the beginning set of spatial frequency patterns. In other aspects, the transition function determination module averages a sum of the user input for each spatial frequency pattern included in the beginning set of spatial frequency patterns and determines the spatial frequency transition function corresponding to the spatial frequency based on the average of the sum of the user input.

A visual neuromodulation system includes a processor and a transition function determination module configured to determine a time duration transition function corresponding to a time duration based on user input. The user input includes: (i) a quantity of illusions perceived in response to viewing a stressful pattern and (ii) a level of discomfort sensed in response to viewing the stressful pattern. The system includes a threshold determination module configured to determine a threshold time duration based on the time duration transition function. The system further includes that, in response to the threshold determination module determining the threshold time duration, a control module determines a display time duration. The stressful pattern is displayed for the display time duration during a predetermined period and the display time duration is greater than the threshold time duration.

In other aspects, the system includes a stressful pattern database. In other aspects, the control module is configured to obtain the stressful pattern from the stressful pattern database. In other aspects, the system includes a storage module configured to maintain an index. In other aspects, each entry of the index includes: (i) a previous user identifier, (ii) a most recent user input of a previous user corresponding to the previous user identifier, and (iii) a most recent display time duration of the previous user. In other aspects, the control module obtains a most recent display time duration of a present user from the storage module and selects the stressful pattern from a stressful pattern database. In other aspects, the transition function determination module, the threshold determination module, the control module, and the storage module are separate processor circuits that execute code.

In other aspects, in response to a new user indicator indicating a present user is new, the control module selects a beginning display time duration as the display time duration. In other aspects, in response to an index entry corresponding to a present user identifier of the present user being included in the storage module, the control module sets a most recent display time duration as the display time duration, selects the stressful pattern, and displays the stressful pattern for the display time duration during the predetermined period. In other aspects, the new user indicator indicates the present user is new when the storage module excludes the index entry corresponding to the present user identifier of the present user. In other aspects, the stressful pattern is displayed for the beginning display time duration during a beginning predetermined period.

In other aspects, in response to a new user indicator indicating a present user is new, a control module cycles through a set of varying time durations during a beginning predetermined period. In other aspects, the cycling includes displaying the stressful pattern for each time duration included in the set of varying time durations and receiving user input for each time duration included in the set of varying time durations. In other aspects, the transition function determination module averages a sum of the user input for each time duration included in the set of varying time durations and determines the time duration transition function based on the average of the sum of the user input.

An individual can independently operate and provide the requested user input for the visual neuromodulation system of the disclosure without the assistance of a medical professional. Further, the individual can use the visual neuromodulation system as directed to improve the individual's tolerance for visually stressful images and, in turn, decrease the likelihood of the individual experiencing visually-induced migraines and/or seizures. Moreover, the visual neuromodulation system is a non-invasive method and prophylactic treatment for decreasing the frequency of visually triggered migraine attacks and/or seizures. The visual neuromodulation system is safe, comfortable, and does not involve the administration of medicine.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Recent functional magnetic resonance imaging (fMRI) studies indicate that visually-induced migraines and/or seizures may be avoided or reduced as a result of a reduced visual cortical hyperexcitability (VCH) within the visual cortex of the brain. To reduce VCH within the visual cortex of the brain, an individual can repeatedly expose themselves to selected threshold stressful patterns to reduce the negative effects of those threshold stressful patterns as well as patterns that are more stressful.

For example, a program or application can identify the threshold stressful pattern for the individual based on feedback from the individual regarding multiple stressful patterns. Once the threshold stressful pattern is identified, the individual can train their vision using the threshold stressful pattern. The threshold stressful pattern varies across individuals. To determine the individual's threshold stressful pattern, the program can prompt the individual for information such as an evaluation of the degree of visual discomfort experienced by the individual when viewing each of the multiple stressful patterns. Alternatively or additionally, the individual can provide another evaluation regarding a number or quantity of visual illusions perceived when viewing each of the multiple stressful patterns.

For example, a striped pattern with spatial frequency (SF) of ~3 cycles per degree (CPD) can induce perceptual illusions and visual discomfort in most people, headaches in patients with migraine, and seizures in patients with photosensitive epilepsy. In contrast, a striped pattern with SF ~0.3 CPD does not induce such effects and is not unpleasant at all to view. The only difference between these stressful and non-stressful striped patterns is the spatial period, suggesting a transition function of the pattern-induced perceptual illusions and visual discomfort with SF. Viewing a stressful pattern for a few seconds induces perceptual illusions and visual discomfort, and prolonged viewing without interruption may trigger headaches in patients with migraine and induce seizures in patients with photosensitive epilepsy. The perception of these visual symptoms, however, diminishes with decreased viewing time, and the symptoms completely vanish when the viewing time is less than a few hundred milliseconds. An appropriately selected SF and/or viewing time may be used to construct a safe, comfortable, and repetitive visual stimulation paradigm to modulate VCH for prophylactic treatment in patients suffering visually triggered headaches or seizures because the adaptation of the brain to the stimulation may result in a reduced VCH.

Figure 1A:
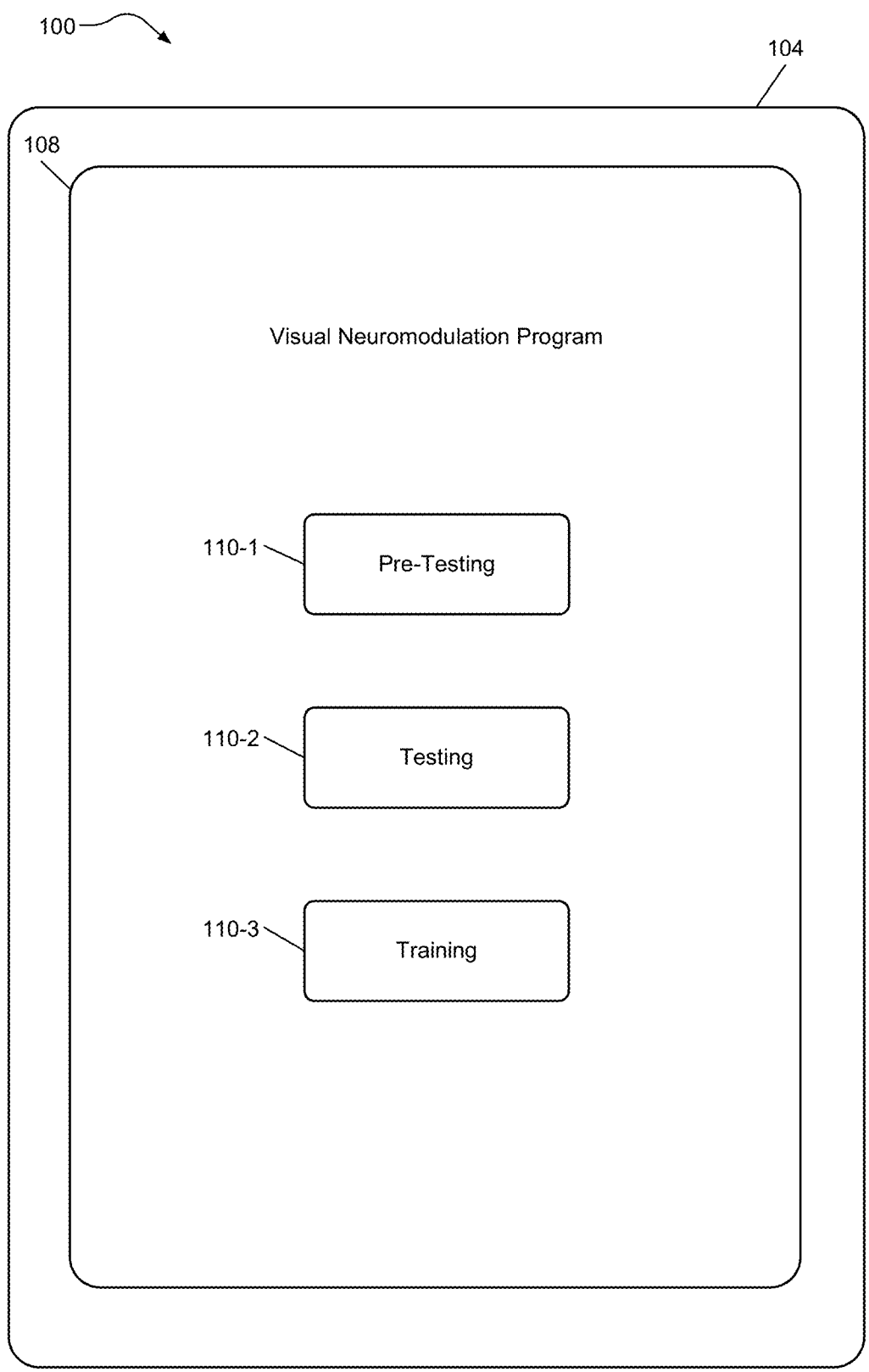
FIG. 1A is a diagrammatic view showing a visual neuromodulation system executed as a visual neuromodulation program displayed on a mobile computing device.

In FIG. 1A, an example visual neuromodulation system 100 executed as a visual neuromodulation program displayed on a mobile computing device 104 is shown. In various implementations, the visual neuromodulation system 100 can be executed on a desktop computer or any other device including a screen, such as a display 108. The mobile computing device 104 can further include a controller that has a memory for storing the series of processes as computer executable instructions and a processor for executing the instructions. The processor performs various computational steps included in the disclosure. The processor does not have to perform all of the computational steps and the individual can perform certain steps. The visual neuromodulation program is stored in the memory of the mobile computing device 104 and executed by the processor. The memory can be a memory circuit that is a non-transitory computer-readable medium.

Upon execution, the visual neuromodulation system 100 includes three options: pre-testing 110-1, testing 110-2, and training 110-3. Upon the individual selecting the user-selectable pre-testing 110-1 button, the visual neuromodulation system 100 will enter a pre-testing mode where the individual is shown black and white striped patterns. The visual neuromodulation system 100 displays instructions on the display 108 explaining how to rate the patterns and identify illusions within the patterns. Upon the individual selecting the user-selectable testing 110-2 button, the visual neuromodulation system 100 will enter a testing mode where the mobile computing device 104 displays multiple patterns on the display 108, and the individual provides two forms of user input: (i) a visual discomfort rating and (ii) a number of illusions perceived.

After the individual provides user input for multiple patterns, the individual can select the user-selectable training 110-3 button. Upon selection of the training button 110-3, the visual neuromodulation system 100 enters a training mode, where, based on the user input during the training mode, the visual neuromodulation system 100 displays a selected pattern to the individual for a first predetermined period to desensitize the individual to the selected pattern. Viewing the selected pattern for the first predetermined period may reduce the visual cortical hyperexcitability (VCH) response in the individual to reduce the likelihood of future visually-induced migraines. Reducing the VCH-response in individuals as well as increasing the individual's tolerance for viewing uncomfortable patterns also results in lowering the likelihood of other future visually-induced reactions, such as seizures. While the remaining disclosure focuses on migraines the same systems and methods assist and prevent other medical conditions.

Figure 1B:
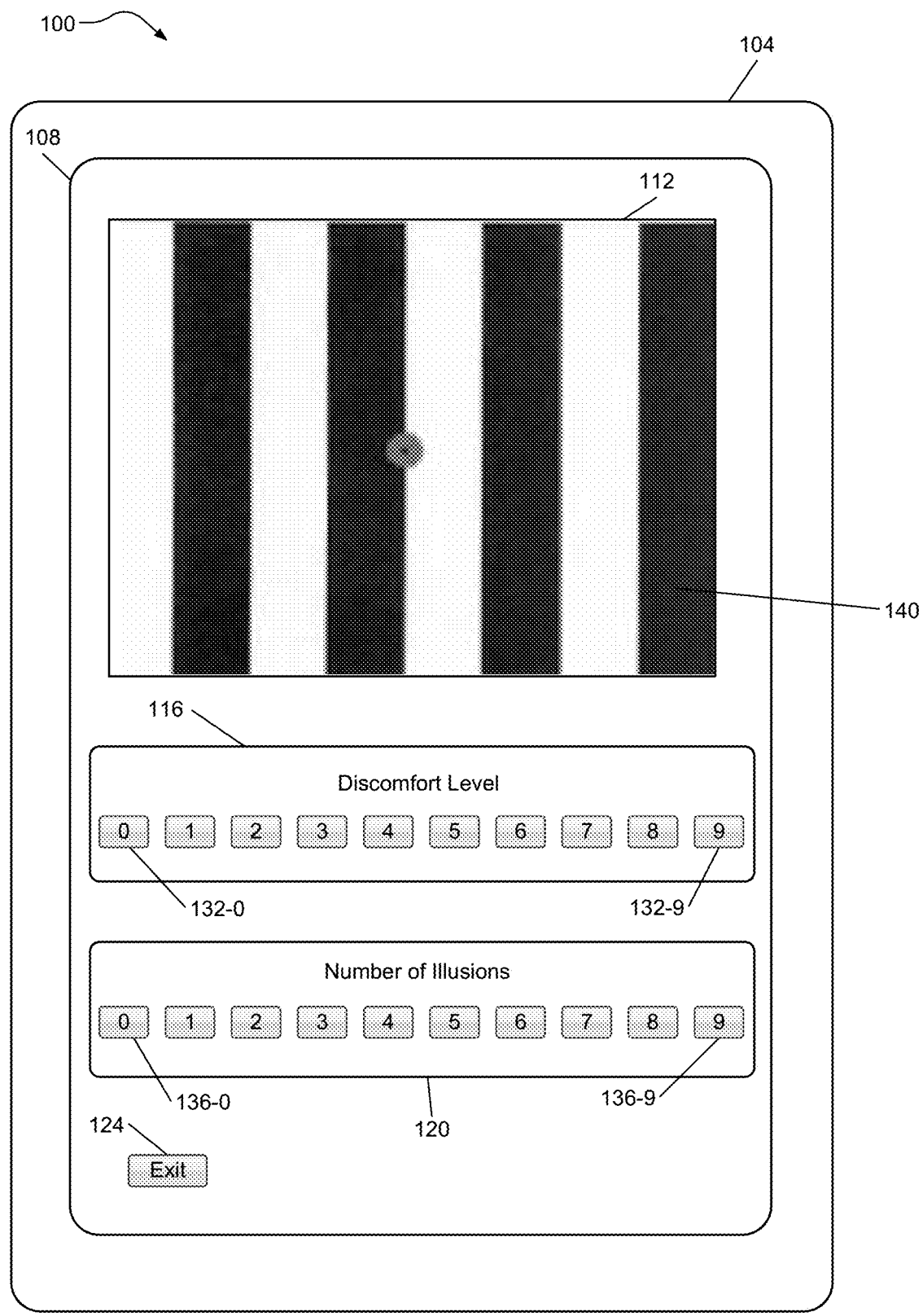
FIG. 1B is a diagrammatic view showing a visual neuromodulation system displayed on the mobile computing device.

In FIG. 1B, an example visual neuromodulation system 100 displayed on the mobile computing device 104 is shown. The mobile computing device 104 can be, for example, a phone, a tablet, or any other device including a processor, a screen, and a rechargeable battery. The display 108 includes a pattern display 112, a visual discomfort scale 116, a number of illusions scale 120, and an exit button 124. The visual discomfort scale 116 includes ratings from level zero, entered by pressing a level zero button 132-0, through level nine, entered by pressing a level nine button 132-9.

The visual discomfort scale 116 may include any number of ratings through level N. The number of illusions scale 120 includes a number zero button 136-0 through a number nine button 136-9. Similarly, the number of illusions scale 120 may include numbers through N. Alternatively, the visual discomfort scale 116 and the number of illusions scale 120 may include radio buttons, a drop down menu, or any other display of inputs for an individual to enter. The exit button 124 exits the visual neuromodulation program.

The pattern display 112 shown in FIG. 1B includes an example pattern. The example pattern is a low spatial frequency (SF) pattern 140. The size of the pattern display 112 and the distance at which the mobile computing device 104 is held from the individual's eyes alters the cycles per degree (CPD) of the SF of patterns. Therefore, throughout the disclosure, the width of the pattern displayed on the pattern display 112 is presumed to be 24 centimeters and the distance the mobile computing device 104 is from the individual's eyes is presumed to be approximately 36 centimeters. To account for the distance between the individual's eyes and the display 108, the visual neuromodulation program will instruct the individual through a prompt on the display 108 to hold the mobile computing device 104 at a specified distance from the individual's eyes. Similarly, when the visual neuromodulation system 100 is on a computing device that is not mobile, the individual will be instructed (through a display prompt) to hold their head at a particular distance from the display 108.

The low SF pattern 140 shown in the pattern display 112 is a black and white striped pattern with a SF of 0.31 CPD. As the SF of the pattern increases, the CPD increase, and the visual discomfort, as well as the number of illusions, increase for an individual with visual cortical hyperexcitability (VCH).

Figure 2:
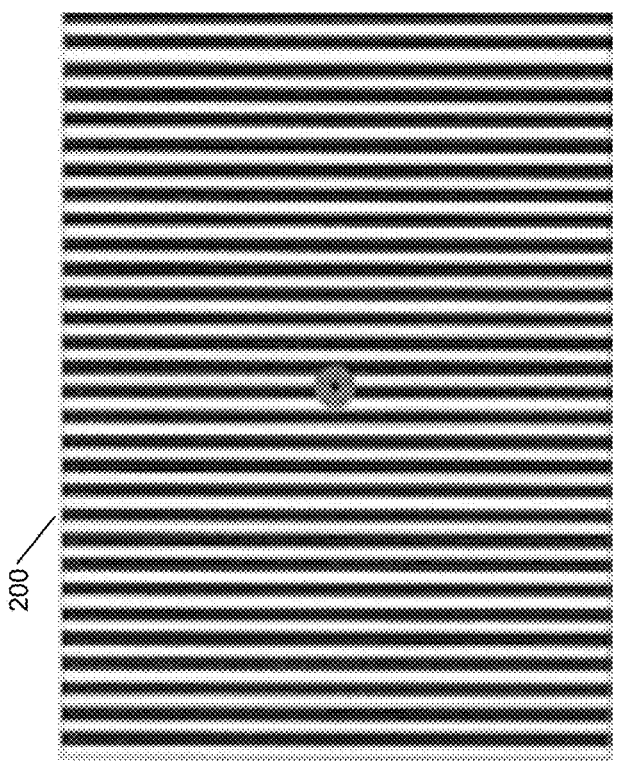
FIG. 2 is a medium spatial frequency (SF) pattern displayed on the mobile computing device.

Furthermore, FIG. 2 shows an example medium SF pattern 200 displayed on the mobile computing device 104. The medium SF pattern 200 has a SF of 2.5 CPD. The individual is most likely to encounter visual discomfort and illusions when viewing the medium SF pattern 200 than when viewing the low SF pattern 140 shown in FIG. 1B.

Figure 3:
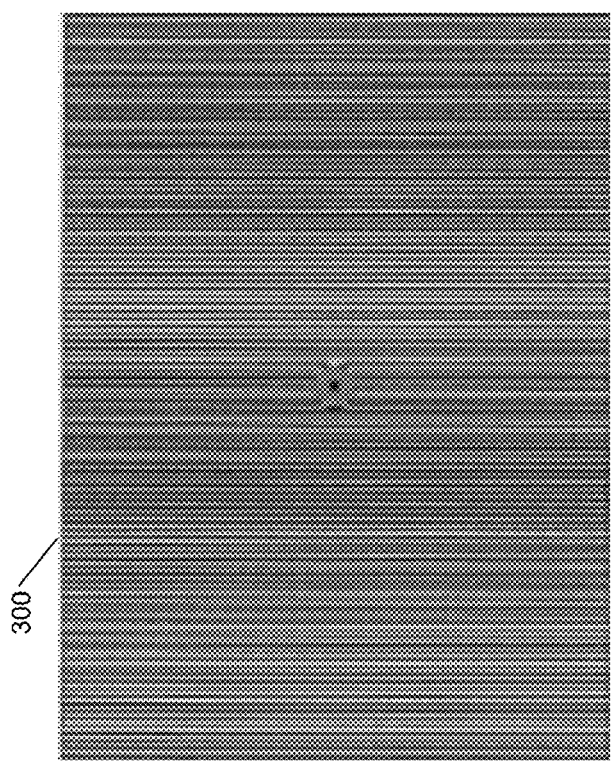
FIG. 3 is a high SF pattern displayed on the mobile computing device.

In FIG. 3, an example high SF pattern 300 displayed on the mobile computing device 104 is shown. The high SF pattern 300 has a SF of 7.9 CPD. The individual is less likely to encounter visual discomfort and illusions when viewing the high SF pattern 300 than when viewing the medium SF pattern 200.

Figure 4:
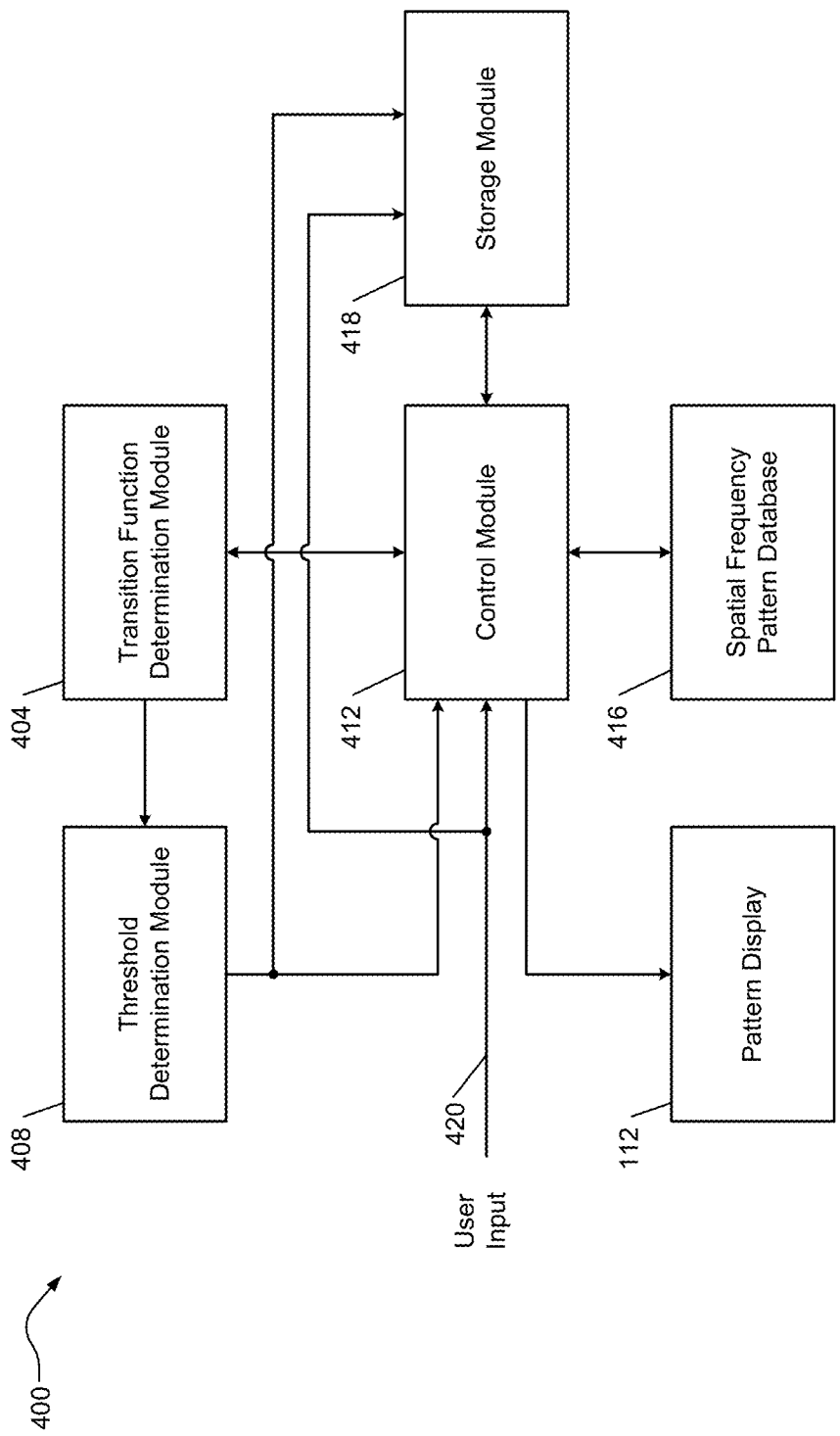
FIG. 4 is a functional block diagram of the visual neuromodulation system.

An example functional block diagram of a visual neuromodulation system 400 is illustrated in FIG. 4. The visual neuromodulation system 400 of FIG. 4 is an example implementations of the visual neuromodulation system 100 in FIGS. 1A and 1B. The visual neuromodulation system 400 includes a transition function determination module 404, a threshold determination module 408, a control module 412, a spatial frequency (SF) pattern and other stressful patterns database 416, and a storage module 418. The transition function determination module 404 is configured to determine a transition function based on user input 420. The visual neuromodulation system 400 determines the transition function to identify an appropriate SF to use during visual stimulation to modulate VCH. That is, to reduce VCH within the visual cortex, VCH modulation is conducted using patterns with a predetermined SF that will not induce a migraine in the individual but contains some low level visual discomfort and/or creates a low likelihood of the individual viewing illusions.

As mentioned with respect to FIG. 1A, the visual neuromodulation system 100 includes the pre-testing 110-1 button where the individual conducts a pre-test. For example, during the pre-test the individual is shown a blank screen for a first predetermined interval, for example, three seconds, on a display 424. In various implementations, the blank screen may be a beginning threshold spatial frequency pattern so the individual does not immediately experience illusions or discomfort due to a spatial frequency being perceived in the display.

The control module 412 can access the SF pattern database 416 and display any pattern contained in the SF pattern database 416 on the display 424 in an order provided by the transition function determination module 404. In various implementations, the control module 412 receives user input 420 and transmits the user input 420 to the transition function determination module 404 where a transition function is calculated. The transition function may correspond to the pattern displayed to the individual in response to the individual perceiving too many illusions or experiencing too much discomfort (for example, a threshold of one illusions may be considered too much as well as any discomfort). However, if the individual did not experience too much discomfort or too many illusions, the transition function determination module 404 may calculate a new transition function as the individual has adapted to the displayed pattern.

The threshold determination module 408 receives the transition function and determines a threshold spatial frequency. The control module 412 receives the threshold spatial frequency and selects a corresponding threshold spatial frequency pattern from the spatial frequency pattern database 416. The control module 412 then instructs the selected threshold spatial frequency pattern to be displayed on the pattern display 112. In this way, the pattern displayed to the individual is updated based on feedback from the individual indicating the individual is adjusting to viewing the pattern without perceiving illusions or experiencing discomfort. In various implementations, the pattern display 112 is implemented as a display screen that may be used to display information other than patterns. The control module 412 also displays patterns on the pattern display 112 of the display 108 of the mobile computing device 104. The display 108 can be a touch screen display configured to receive user input 420 by touching, tapping, sliding, etc., the display 108.

The individual is then shown a striped pattern, such as the low SF pattern 140 of FIG. 1B, for a second predetermined interval, for example, four seconds. The individual is shown the blank screen again for the first predetermined interval. Then, the individual is shown a stressful striped pattern, such as the medium SF pattern 200 of FIG. 2, for the second predetermined interval. In various implementations, the first predetermined interval and the second predetermined interval do not have to be equal.

After viewing the stressful striped pattern, the individual rates the visual discomfort experienced when viewing each striped pattern on a scale of 0-9, where 0 represents no discomfort and 9 represents a maximum discomfort. In FIG. 1B, the individual enters their visual discomfort rating (0-9) using buttons indicating the level of discomfort (132-0-132-9) on the visual discomfort scale 116.

Additionally, after viewing each striped pattern, the individual determines whether any illusions were perceived. For example, the illusions can include (i) blurring lines, (ii) zig-zag lines, (iii) wavering or moving lines and/or patterns, (iv) flickering spots and/or lines, (v) colors (for example, red, green, blue, or yellow), or (vi) any other undefined illusion. The individual enters the number of illusions seen using the numbered buttons (136-0-136-9) on the number of illusions scale 120. The user input 420 includes the button pressed on the visual discomfort scale 116 and the button pressed on the number of illusions scale 120 for each pattern displayed on the pattern display 112. After the individual makes a selection on the visual discomfort scale 116 and the number of illusions scale 120, the transition function determination module 404 automatically prompts the control module 412 to display the next striped pattern on the pattern display 112.

During the pre-test, the individual is shown the pre-test patterns and prompted to rate the visual discomfort and the number of illusions seen. The visual neuromodulation system 400 can display instructions during the pre-test describing how to rate visual discomfort as well as defining visual illusions for the individual to identify. After the pattern display 112 displays the pre-test patterns and displays instructional prompts to the individual, the pattern display 112 displays the pre-test patterns a second time to confirm the individual's rating of discomfort and number of illusions perceived.

The pre-test continues to display to the individual multiple patterns on the pattern display 112 according to the control module 412. Each pattern displayed will have a different SF. For example, the SF can range from 0.27 CPD through 2.80 CPD. For example, the different SF patterns can include 0.27, 0.40, 0.53, 0.71, 0.89, 1.7, 1.42, 1.77, 2.13, and 2.80 CPD. The multiple patterns are displayed to the individual sequentially and in increasing CPD order. Alternatively, the control module 412 can display the multiple patterns on the pattern display 112 in any order. The multiple patterns are displayed to the individual for the individual to identify discomfort and illusions that may occur prior to testing.

Once the individual completes the pre-test, the individual can select the testing 110-2 button shown in FIG. 1A. When in testing mode, the control module 412 displays, using the pattern display 112, multiple patterns, for example, the ten patterns previously discussed ranging from 0.27 CPD through 2.80 CPD. The pattern display 112 first displays a blank screen for a third predetermined interval, for example, three seconds. Then, the pattern display 112 displays the pattern with the lowest SF (for example, 0.27 CPD) for a fourth predetermined interval, for example, two seconds. The individual then rates any visual discomfort and identifies the number of illusions perceived. The pattern display 112 then displays the blank screen for another third predetermined interval and the next higher SF pattern (for example, 0.40 CPD) for another fourth predetermined interval.

The visual neuromodulation system 400 cycles sequentially through the ten patterns and the individual provides user input 420 (amount of visual discomfort and number of illusions perceived) for each pattern. Each pattern is cycled through ten times and user input 420 is received for each pattern ten times. Once all the user input 420 is received, the transition function determination module 404 can average the data for each pattern. Alternatively, the transition function determination module 404 can select the highest user input 420 for each pattern to determine the transition function.

The threshold determination module 408 is configured to determine a threshold SF pattern based on the transition function where the visual neuromodulation should begin. The threshold SF pattern is a pattern that reliably provokes visual discomfort and/or illusions and is well-tolerable for the individual to view for an extended period of time, for example, 25 minutes, to gradually adapt to prolonged visual stimulation. The individual views the threshold SF pattern for the extended period of time on a daily basis to reduce VCH in the visual cortex and gradually adapt to prolonged visual stimulation and consequently reduce the VCH-response to the threshold SF pattern (that is, reduce the likelihood of the threshold SF triggering visually-induced migraines).

For individual training, the individual accesses the visual neuromodulation program on their mobile computing device 104 and selects the training 110-3 button shown in FIG. 1A. The storage module 418 stores the threshold SF once the threshold determination module 408 selects the threshold SF for the individual. The storage module 418 also receives and stores the user input 420 to maintain a record of the number of illusions and any visual discomfort experienced with each pattern displayed. The individual then uses the visual neuromodulation system 400 to train their visual cortex to reduce VCH-response to the selected threshold SF by prolonged exposure to the threshold SF. For example, the individual can train by viewing the threshold SF pattern for the first predetermined period, for example, 25 minutes each day. Alternatively, the training can include viewing the threshold SF pattern for a shorter or longer period each training session and/or the training may skip certain days.

After the individual has conducted the training for a second predetermined period, for example, one month, the visual neuromodulation system 400 selects the pattern with a SF sequentially higher than the threshold SF pattern as the new threshold SF pattern. The individual then trains using the new threshold SF pattern. The second predetermined period is chosen as the amount of time it will take the individual to adapt to the threshold SF pattern. That is, the second predetermined period is the amount of time it will take the individual to no longer experience discomfort and/or the amount of time it will take for the illusions to be significantly reduced to a normal level when viewing the threshold SF pattern.

In various implementations, the visual neuromodulation system 400 can reduce the VCH-response and gradually adapt the individual to a stressful pattern using variable time duration instead of the variable SF. That is, the individual can view the stressful pattern for a selected threshold time duration to adapt to the pattern. Once adapted, a longer threshold time duration may be selected according to the threshold determination module 408 for the individual to adapt to the stressful pattern. The threshold time duration can be increased until the individual no longer experiences discomfort and/or the illusions are significantly reduced to a normal level when the individual views the stressful pattern.

The visual neuromodulation system 400 can incorporate into the visual neuromodulation program a selection prior to the screen shown in FIG. 1A, where the individual can select using a SF factor or a time duration (TD) factor to adapt the individual's visual cortex to certain patterns that can trigger migraines. Additionally, while the black and white striped pattern is shown as visual stimuli, a variety of patterns may be used to induce visual discomfort and/or illusions. Most patterns may be used to reduce the VCH-response as long as the selected pattern is displayed to the individual through the visual neuromodulation program for an appropriately selected viewing time or time duration.

In various implementations, the subsequent threshold SF pattern is automatically selected after the training is completed for the second predetermined period. Alternatively, the individual can repeat the testing after the training is completed (that is, after the second predetermined interval). In this way, the threshold SF pattern will not increase unless the user is experiencing less discomfort or fewer illusions. The individual can return to testing mode by selecting the testing 110-2 button shown in FIG. 1A. In various implementations, after the second predetermined period the visual neuromodulation system 400 will automatically request the individual conduct the testing again.

Figure 5:
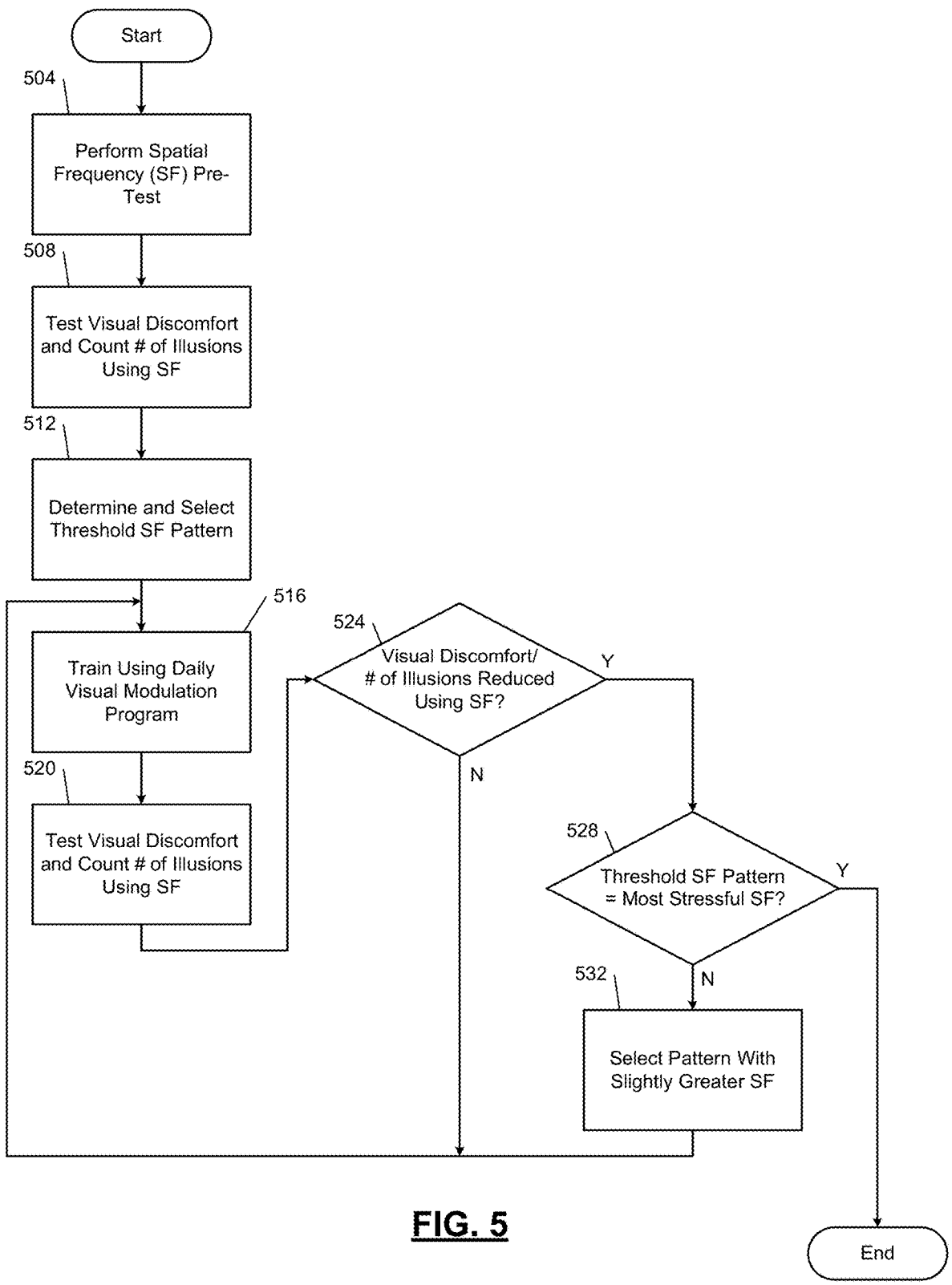
FIG. 5 is a flowchart depicting an implementation of the visual neuromodulation system based on SF.

In FIG. 5, a flowchart depicting an implementation of the visual neuromodulation system 100 based on SF is shown. The visual neuromodulation system 100 includes a SF visual neuromodulation program, as shown in FIG. 5, which is stored in the memory of the mobile computing device 104 and executed by the processor.

Control begins at 504 where the pre-test is performed for patterns with varying SF. As mentioned previously, the individual may have selected the visual neuromodulation program with varying SF. After the pre-test is completed at 504, control continues to 508 to perform the test. At 508, the individual is exposed to multiple patterns with varying SF multiple times and prompted to rate each pattern each time the visual neuromodulation system 100 displays the pattern. The individual is also prompted to count and report how many illusions are seen with each pattern each time the pattern is displayed. Based on the user input (visual discomfort rating and number of illusions perceived), the transition function determination module 404 determines the transition function.

After the test is completed in 508, control continues to 512 where the threshold determination module 408 of FIG. 4 determines the threshold SF pattern. As mentioned previously, the threshold SF pattern is selected based on transition function. The threshold SF pattern is the pattern that induces low level visual discomfort and/or causes the individual to perceive very few illusions. The threshold SF pattern is tolerable for the individual to view for a prolonged time and causes some discomfort and/or illusions causing the individual to adjust and adapt to the threshold SF pattern.

Once the threshold SF pattern is determined and selected at 512, the training using the daily visual modulation program is performed at 516. The daily visual modulation program is the individual training their vision. The individual launches the visual neuromodulation program on the mobile computing device 104 and selects the training 110-3 button option. The visual neuromodulation system 100 displays the threshold SF pattern on the display 108 (specifically, within the pattern display 112) for the first predetermined period, for example, 25 minutes, with the pattern on-and-off, for example, two seconds on followed by two seconds off and repeat again. The daily visual neuromodulation program is continued for the second predetermined period, for example, one month.

Once the training is completed in 516, the visual neuromodulation system 100 returns to testing at 520 to determine the visual discomfort and number of illusions perceived after training. The transition function determination module 404 determines the transition function and the threshold determination module 408 identifies a new threshold SF pattern.

At 524, the storage module 418 compares the original rating and number of illusions perceived of the threshold SF pattern to the current rating and number of illusions perceived of the threshold SF pattern to determine if the visual discomfort or the number of illusions have decreased. Alternatively, the storage module 418 can compare the threshold SF pattern to the new threshold SF pattern to determine whether the visual discomfort and/or number of illusions have been reduced. If control determines at 524 that the visual discomfort or the number have illusions have not decreased, control returns to 516 to continue with the current training.

Instead, if control determines at 524 that the visual discomfort or the number of illusions has decreased, control continues to 528. At 528, control determines whether the SF of the threshold SF pattern is the most stressful SF. If the threshold SF pattern is the most stressful SF, control ends. However, if the threshold SF pattern is not the most stressful SF, control continues to 532 to increase the SF. That is, the sequentially increased SF pattern is set as the threshold SF pattern, and control continues to 516 to train using the new and increased threshold SF pattern.

Figure 6:
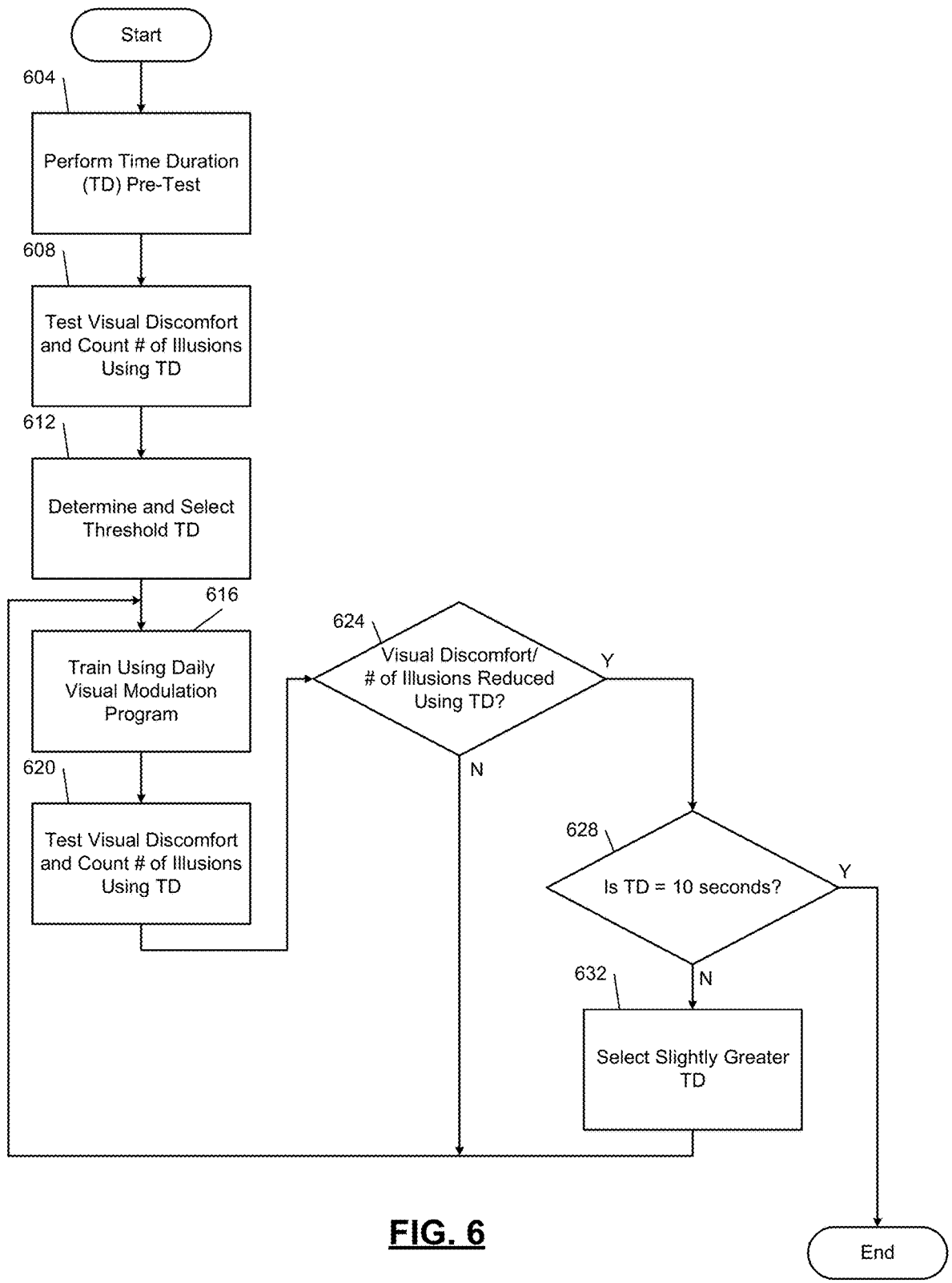
FIG. 6 is a flowchart depicting an alternative implementation of the visual neuromodulation system based on time duration.

In FIG. 6, a flowchart depicting an implementation of a visual neuromodulation system based on time duration is shown. The visual neuromodulation system 100 includes a time duration (recited as TD in the flowchart) visual neuromodulation program, as shown in FIG. 6, which is stored in the memory of the mobile computing device 104 and executed by the processor.

Control begins at 604 where the pre-test is performed based on time duration. The same pre-test is conducted, however, the mobile computing device 104 prompts instructional information regarding the time duration of a stressful pattern. That is, the stressful pattern is displayed to the display 108 of the mobile computing device 104 for predetermined amounts of time. For example, the stressful pattern is displayed using the display 108 for 100 milliseconds, one second, two seconds, and continuing up to ten seconds. After the time duration instructions are completed during the pre-test at 604, control continues to 608 to perform the test.

At 608, the test displays the stressful pattern multiple times for varying and increasing amounts of time, with a blank screen in between each display of the stressful pattern. After the stressful pattern is displayed each time, the individual is prompted to rate the visual discomfort of the stressful pattern as well as record the number of illusions perceived. Cycling through the stressful pattern for multiple time durations can occur, for example, ten times, recording the user input 420 for each display of the stressful pattern. Once all the user input 420 is received, the transition function determination module 404 determines the transition function based on the user input 420. Control continues to 616 where the threshold determination module 408 determines a threshold time duration.

Control continues to 616 to train using the daily visual neuromodulation program. As discussed previously, at 616 the training is performed for the visual cortex of the individual to adapt to the stressful pattern being displayed for the threshold time duration. After the daily visual neuromodulation program has been conducted for the second predetermined period, for example, one month, control continues to 620 to return to testing.

At 620, the visual neuromodulation system 100 tests the individual. Then, at 624, control determines whether the visual discomfort has reduced or the number of illusions perceived by the individual has reduced. That is, the individual completes the testing and the transition function determination module 404 determines a new transition function. Based on the new user input 420, the storage module compares the new user input to the previous user input to determine whether the individual experienced reduced visual discomfort and/or fewer illusions. If 624 is false, control returns to 616 to train using the same threshold time duration. However, if 624 is true, control continues to 628 to determine if the threshold time duration is ten seconds. If 628 is true, control ends. However, if 628 is false, control continues to 632 to increase the threshold time duration, for example, by one second. Control then continues to 616 to train using the new threshold time duration.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip. While various embodiments have been disclosed, other variations may be employed. All of the components and function may be interchanged in various combinations. It is intended by the following claims to cover these and any other departures from the disclosed embodiments which fall within the true spirit of this invention.

What is claimed is:

1. A visual neuromodulation system comprising:
   a processor;
   a transition function determination module configured to determine a spatial frequency transition function corresponding to a spatial frequency based on user input, wherein the user input includes:
      (i) a quantity of illusions perceived in response to viewing a spatial frequency pattern associated with the spatial frequency; and
      (ii) a level of discomfort sensed in response to viewing the spatial frequency pattern associated with the spatial frequency;
   a threshold determination module configured to determine a threshold spatial frequency based on the spatial frequency transition function; and
   in response to the threshold determination module determining the threshold spatial frequency, a control module selects a display spatial frequency pattern from a set of spatial frequency patterns, and wherein the selected spatial frequency pattern corresponds to a display spatial frequency greater than the threshold spatial frequency to display for a predetermined period.

2. The visual neuromodulation system of claim 1 further comprising a spatial frequency pattern database, wherein the control module is configured to obtain the selected spatial frequency pattern corresponding to the display spatial frequency from the spatial frequency pattern database.

3. The visual neuromodulation system of claim 1 further comprising a storage module configured to maintain an index, wherein each entry of the index includes: (i) a previous user identifier, (ii) a most recent user input of a previous user corresponding to the previous user identifier, and (iii) a most recent selected spatial frequency of the previous user.

4. The visual neuromodulation system of claim 3 wherein the control module obtains a most recent selected spatial frequency of a present user from the storage module and selects a corresponding most recent selected spatial frequency pattern from a spatial frequency pattern database.

5. The visual neuromodulation system of claim 3 wherein the transition function determination module, the threshold determination module, the control module, and the storage module are separate processor circuits that execute code.

6. The visual neuromodulation system of claim 3 wherein:
in response to a new user indicator indicating a present user is new, the control module selects a beginning spatial frequency pattern as the spatial frequency pattern; and
in response to an index entry corresponding to a present user identifier of the present user being included in the storage module, the control module sets a most recent selected spatial frequency as the spatial frequency, selects a most recent selected spatial frequency pattern corresponding to the most recent selected spatial frequency, and displays the most recent selected spatial frequency pattern for the predetermined period.

7. The visual neuromodulation system of claim 6 wherein the new user indicator indicates the present user is new when the storage module excludes the index entry corresponding to the present user identifier of the present user.

8. The visual neuromodulation system of claim 6 wherein the beginning spatial frequency pattern is displayed for a beginning predetermined period.

9. The visual neuromodulation system of claim 1 wherein, in response to a new user indicator indicating a present user is new, a control module cycles through a beginning set of spatial frequency patterns, and wherein the cycling includes:
displaying each spatial frequency pattern included in the beginning set of spatial frequency patterns for the predetermined period; and
receiving user input for each spatial frequency pattern included in the beginning set of spatial frequency patterns.

10. The visual neuromodulation system of claim 9 wherein the transition function determination module averages a sum of the user input for each spatial frequency pattern included in the beginning set of spatial frequency patterns and determines the spatial frequency transition function corresponding to the spatial frequency based on the average of the sum of the user input.

11. A visual neuromodulation system comprising:
a processor;
a transition function determination module configured to determine a time duration transition function corresponding to a time duration based on user input, wherein the user input includes:
(i) a quantity of illusions perceived in response to viewing a stressful pattern; and
(ii) a level of discomfort sensed in response to viewing the stressful pattern;
a threshold determination module configured to determine a threshold time duration based on the time duration transition function; and
in response to the threshold determination module determining the threshold time duration, a control module determines a display time duration, wherein the stressful pattern is displayed for the display time duration during a predetermined period, and wherein the display time duration is greater than the threshold time duration.

12. The visual neuromodulation system of claim 11 further comprising a stressful pattern database, wherein the control module is configured to obtain the stressful pattern from the stressful pattern database.

13. The visual neuromodulation system of claim 11 further comprising a storage module configured to maintain an index, wherein each entry of the index includes: (i) a previous user identifier, (ii) a most recent user input of a previous user corresponding to the previous user identifier, and (iii) a most recent display time duration of the previous user.

14. The visual neuromodulation system of claim 13 wherein the control module obtains a most recent display time duration of a present user from the storage module and selects the stressful pattern from a stressful pattern database.

15. The visual neuromodulation system of claim 13 wherein the transition function determination module, the threshold determination module, the control module, and the storage module are separate processor circuits that execute code.

16. The visual neuromodulation system of claim 13 wherein:
in response to a new user indicator indicating a present user is new, the control module selects a beginning display time duration as the display time duration; and
in response to an index entry corresponding to a present user identifier of the present user being included in the storage module, the control module sets a most recent display time duration as the display time duration, selects the stressful pattern, and displays the stressful pattern for the display time duration during the predetermined period.

17. The visual neuromodulation system of claim 16 wherein the new user indicator indicates the present user is new when the storage module excludes the index entry corresponding to the present user identifier of the present user.

18. The visual neuromodulation system of claim 16 wherein the stressful pattern is displayed for the beginning display time duration during a beginning predetermined period.

19. The visual neuromodulation system of claim 11 wherein, in response to a new user indicator indicating a present user is new, a control module cycles through a set of varying time durations during a beginning predetermined period, and wherein the cycling includes:
displaying the stressful pattern for each time duration included in the set of varying time durations; and
receiving user input for each time duration included in the set of varying time durations.

20. The visual neuromodulation system of claim 19 wherein the transition function determination module averages a sum of the user input for each time duration included in the set of varying time durations and determines the time duration transition function based on the average of the sum of the user input.

* * * * *